(12) United States Patent
Ramakrishna et al.

(10) Patent No.: US 10,858,622 B2
(45) Date of Patent: Dec. 8, 2020

(54) HEATSEAL SAMPLING

(71) Applicant: Global Life Sciences Solutions USA LLC, Marlborough, MA (US)

(72) Inventors: Manoj Ramakrishna, Bangalore (IN); Haresh Digambar Patil, Bangalore (IN); Sebastian John, Bangalore (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 220 days.

(21) Appl. No.: 15/744,152

(22) PCT Filed: Aug. 12, 2016

(86) PCT No.: PCT/EP2016/069299
§ 371 (c)(1),
(2) Date: Jan. 12, 2018

(87) PCT Pub. No.: WO2017/025641
PCT Pub. Date: Feb. 16, 2017

(65) Prior Publication Data
US 2018/0201894 A1    Jul. 19, 2018

(30) Foreign Application Priority Data

Aug. 13, 2015 (IN) ............................ 2499/DEL/2015
Jan. 8, 2016 (GB) .................................. 1600315.4

(51) Int. Cl.
*C12M 1/26* (2006.01)
*C12M 1/12* (2006.01)
*C12M 1/28* (2006.01)

(52) U.S. Cl.
CPC ............ *C12M 33/04* (2013.01); *C12M 1/121* (2013.01); *C12M 1/28* (2013.01); *C12M 33/00* (2013.01); *C12M 37/04* (2013.01)

(58) Field of Classification Search
CPC ........ C12M 33/04; C12M 33/00; C12M 1/28; C12M 1/121; C12M 37/04
See application file for complete search history.

(56) References Cited

U.S. PATENT DOCUMENTS 4,023,607 A * 5/1977 Jensen ................. A61F 5/44
383/127
4,937,194 A   6/1990 Pattillo et al.
(Continued)

FOREIGN PATENT DOCUMENTS

DE    10356616 A1    6/2005
WO    1990/09431 A1    8/1990
(Continued)

OTHER PUBLICATIONS

PCT International Search Report and Written Opinion for PCT Application No. PCT/EP2016/069299 dated Nov. 2, 2016 (11 pages).

*Primary Examiner* — Michael L Hobbs
(74) *Attorney, Agent, or Firm* — Eversheds Sutherland (US) LLP

(57) ABSTRACT

The present invention provides a device and method for sampling from a cell culture bioreactor. The invention is useful where it is required to determine the cell count, provide a sample for off-line analyses or remove a sample while at the same time retain sterility of the sample for quality control (QC) assessment. The device of the invention allows for facile aseptic sampling at one or more instances in time during a cell expansion in a bioreactor.

22 Claims, 11 Drawing Sheets

(56) References Cited

U.S. PATENT DOCUMENTS

| | | | |
|---|---|---|---|
| 5,350,080 A * | 9/1994 | Brown | C12M 99/00 |
| | | | 220/62.21 |
| 2008/0166705 A1 * | 7/2008 | Schwoebel | C12Q 1/6825 |
| | | | 435/6.12 |
| 2008/0213894 A1 | 9/2008 | Antwiler | |
| 2013/0017127 A1 * | 1/2013 | Tokumaru | C12M 23/10 |
| | | | 422/509 |
| 2014/0051162 A1 | 2/2014 | Nankervis | |
| 2014/0123775 A1 | 5/2014 | Newbold et al. | |
| 2017/0202740 A1 * | 7/2017 | Yoshida | B32B 27/36 |

FOREIGN PATENT DOCUMENTS

| | | | |
|---|---|---|---|
| WO | 2002/28996 A1 | 4/2002 | |
| WO | 2009/158416 A2 | 12/2009 | |
| WO | 2011/038008 A2 | 3/2011 | |
| WO | WO 2011/038008 A2 * | 3/2011 | C12M 33/00 |
| WO | WO-2011038008 A2 * | 3/2011 | C12M 37/00 |
| WO | 2013/130176 A1 | 9/2013 | |

* cited by examiner

HEATSEAL SAMPLING

CROSS REFERENCE TO RELATED APPLICATIONS

This application claims the priority benefit of PCT/EP2016/069299 filed on Aug. 12, 2016 which claims priority benefit of India Application No. 2499/DEL/2015 filed Aug. 13, 2015 and Great Britain Application No. 1600315.4 filed Jan. 8, 2016. The entire contents of which are hereby incorporated by reference herein.

TECHNICAL FIELD OF THE INVENTION

The present invention relates to a device and method for sampling cells from a cell culture in a bioreactor. Applications of the invention include determining cell count, providing a sample for off-line analyses or removing a sample while retaining its sterility for quality control (QC) assessment. More particularly, the invention relates to a method for aseptic sampling of cells at one or more instances in time during a cell expansion in a bioreactor.

DESCRIPTION OF RELATED ART

Flexible cell culture bags are currently in widespread use for the culture and expansion of a variety of cell products. High cell densities are achieved by using media perfusion, where fresh media is added to the culture and spent media is removed. The rate of media perfusion is dependent upon the concentration of cells within the cell bag, the perfusion rate increasing with increased cell concentration. Over the course of the cell expansion the operator may wish to understand what is happening with the cell culture environment, including for example the supply of nutrients and accumulation of waste metabolites. A sample from the cell bag for further analysis is taken, generally at more than one timepoint, in order to monitor the growth rate and concentration of the cultured cells. However, known sampling methods include multiple steps requiring a skilled operator and which are not without risk of contaminating the cell culture and/or the sample.

One method for sampling is to connect a syringe to a needless port of the bioreactor and to withdraw a sample of the cell suspension into the syringe. To ensure sterility is maintained, this sampling technique requires care in particular because a syringe is a two-way device with the potential to allow the operator to push air into the bioreactor and risk contaminating the culture. Furthermore, disconnection of the syringe from the bioreactor after sampling exposes the contents of the syringe to the local environment and increases the risk of microbial contamination.

In another known method the user may fit a length of sterile tube to a 3-way valve on the cell bag to which a syringe can be fitted in order to withdraw a sample from the cell bag into the tubing. The tubing is then clamped and sealed to provide a sterile cell sample. Opening the sampling port exposes the culture to the external environment which carries the risk of contamination of the culture, and each sampling instance requires drawing a portion of the sample from the cell bag. Any leakage or contamination in the tubing or in the connection between the culture vessel and the tubing may introduce contamination in the cell bag. Every sampling instance is accompanied by a user attaching some sort of tubing either directly or indirectly to the cell bag, thereby increasing the risk of contamination of the cell culture. There is also a likelihood of a portion of the sample being left in the tubing after the sampling instance. This residual sample may then be inadvertently carried over to the next sampling instance, thereby jeopardizing the purity of the sample obtained in the next sampling instance.

Current methods to carry out sampling from a bioreactor can be cumbersome and can leave the isolated sample exposed to the atmosphere. Sampling the bioreactor using known approaches also runs the risk of providing a non-sterile sample that may fail the sterility QC check. In addition to the complex nature and risk of contamination associated with known sampling techniques, there also may exist an inherent limitation on the number or frequency of samplings which may be accommodated, either by reason of a limited number of sterilisable sequences to which a particular connector can be subjected to before severe degradation occurs or simply by reason of the long time needed to perform a sample withdrawal. These limitations may pose significant problems in situations where rapid and frequent sampling is required in order to monitor a potentially fast-changing situation. Still further, of course, elaborate and/or time-consuming sampling techniques can add significantly to the overall cost of the culture process.

Automated sterile sampling solutions are in great demand in the field of cell therapy. As the known solutions are very laborious and typically involve dangling tubes and holders, there is a need for a more compact, easily automatable and completely sterile solution that overcomes the above-described problems.

SUMMARY OF THE INVENTION

In a first aspect the present invention provides a device (1) for taking a sample from a liquid cell culture in a bioreactor (2) wherein said device (1) comprises:
  (i) a hollow body (3) comprising outer walls (4) that define a fluid path (5a-5b) therethrough wherein said outer walls (4) are at least partly comprised of a sealable material, wherein said fluid path (5a-5b) begins at an upstream end (6a) and ends at a downstream end (6b) of said hollow body (3), and wherein said upstream and downstream ends (6a, 6b) are adapted to fluidly connect said fluid path (5a-5b) with the interior (2i) of said bioreactor (2); and,
  (ii) a sealing means (7) which is adapted to seal the perimeter of a section (8) of said sealable material without blocking said fluid path (5a-5b), wherein said sealing means (7) is moveable between different portions of said outer walls (4).

In a second aspect the present invention provides a method for taking a sample from a bioreactor (2) containing a liquid cell culture wherein said method comprises:
  (a) providing a device (1) as defined herein fluidly connected to said bioreactor (2); and,
  (b) activating said sealing means (7) to seal a section (8b) of said sealable material without blocking said fluid path (5a-5b) wherein said section contains a sample of said liquid cell culture.

The present invention provides a readily automatable method for rapid cell sampling which will maintain a sterile sample, reduce handling time and effort compared to prior art. The device of the invention can be provided as a pre-sterile single ready to use disposable sampling kit, which is easy for the operator to handle.

The method of the invention allows multi-sampling in a manner that is advantageous compared with prior art multi-sampling methods and systems.

The method of the invention is a simple, low risk and effective procedure to collect one or more samples from any bioreactor. Recirculating fluid flow is used so that there are no losses of the cell culture during sampling. With the method of the invention each sample is separated from the remainder of the system so that there is no cross contamination during each sampling.

It is also possible to set the device of the invention to carry out automatic sampling at set periodic intervals. Furthermore, the device of the invention is scalable and compatible with any type of cell culture system and requires minimal or no human intervention in sampling.

DETAILED DESCRIPTION OF THE PREFERRED EMBODIMENTS

Figure 1:
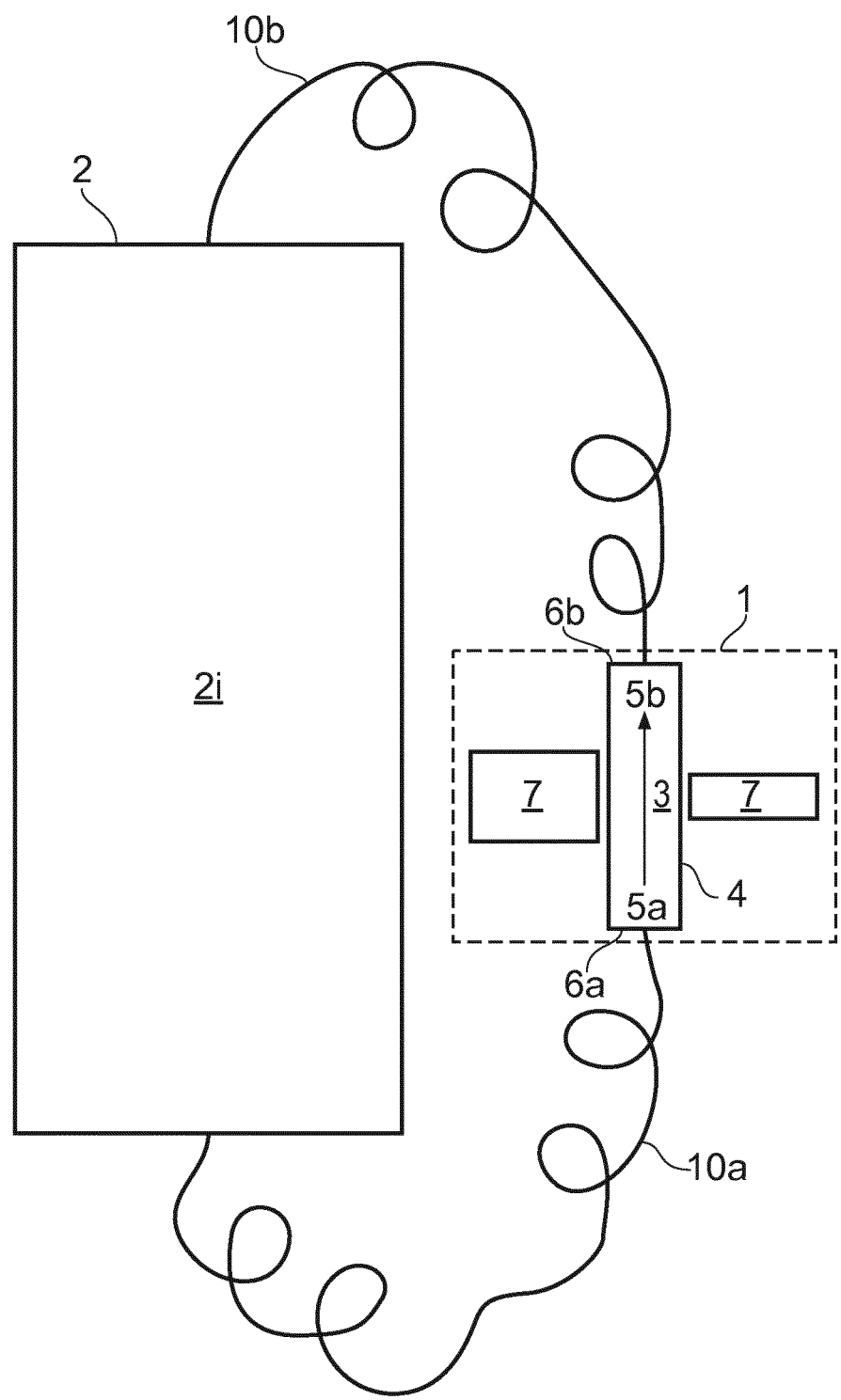
FIG. 1 shows an exemplary device (1) of the invention where the hollow body (3) of the device is fluidly connected to the interior (2i) of a bioreactor (2).

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that other features may be present in addition. The term 'comprising' includes as a preferred subset "consisting essentially of" which means that the composition has the components listed without other features or components being present.

The term "sample" in the context of the present invention refers to a representative portion of a liquid cell culture in a bioreactor, which when analysed provides an accurate reflection of the cell culture environment at a particular point in time allowing monitoring of the growth rate and concentration of the cultured cells.

The term "liquid cell culture" refers to a liquid growth medium in which cells separated from their original in vivo source are suspended and which is subjected to conditions favourable for proliferation of the cells through multiple generations.

The term "bioreactor" refers to any manufactured or engineered device or system that supports an in vitro biologically active environment. A bioreactor in the context of the present invention is a device or system in which cells or tissues are grown in the context of a liquid cell culture. The bioreactor may be a rigid reusable vessel made e.g. from stainless steel or a flexible cell bag designed for a single use before being discarded.

The "hollow body" of the device of the invention is any container that can be adapted to be fluidly connected to a bioreactor so that a liquid cell culture in said bioreactor can flow continuously through said hollow body without disrupting the growth of the cell culture. The "outer walls" of the hollow body can be formed of any liquid-tight material compatible with containing a cell culture as long as at least part of the liquid-tight material is also a sealable material. The term "sealable material" refers to any material that can be sealed in a liquid-tight manner either to itself or to another material comprised in the outer walls.

The terms "upstream" and "downstream" take their ordinary meaning, i.e. where upstream is where flow enters and downstream where flow exits the device of the invention.

The term "fluidly connect" refers to a connection made between two or more components where liquid flow is permitted from the interior of one component to the interior of one or more other components but not from the inside out or from the outside in.

The term "sealing means" refers to any means capable of isolating a section of the hollow body by sealing a portion of the sealable material of the device. The portion that is sealed forms a perimeter of a three-dimensional volume of cell culture medium isolated from the rest of the cell culture medium. Liquid flow from the bioreactor through the device cannot enter the sealed section.

The term "without impeding" means that flow of liquid cell culture through the device can continue even after sealing a section of the sealable material.

The term "moveable" in the context of the sealing means it is capable of changing position about the hollow body of the device, primarily to permit multiple sampling.

The internal surfaces of the device of the invention that come into contact with the liquid cell culture from the bioreactor should be made from materials compatible with cell cultures. Suitable materials are well-known to those of skill in the art. Non-limiting examples of suitable materials include stainless steel and a variety of plastics.

In one embodiment of the device (1) of the invention as schematically illustrated in FIG. 1, an upstream conduit (10a) fluidly connects the interior (2i) of said bioreactor (2) with said fluid path (5a, 5b) via said upstream end (6a) of said device (1) and a downstream conduit (10b) fluidly connects the interior (2i) of said bioreactor (2) with said fluid path (5a, 5b) via said downstream end (6b) of said device (1).

In one embodiment of the device (1) for example as illustrated in FIG. 1 said upstream conduit (10a) and said downstream conduit (10b) are formed from plastic tubing. In one embodiment said plastic tubing is flexible plastic tubing. Non-limiting examples of flexible plastic tubing materials include polypropylene (PP), polyethylene (PE), polyvinyl chloride (PVC), nylon, polytetrafluoroethylene (PTFE) and polyether ketone (PEEK).

Figure 2:
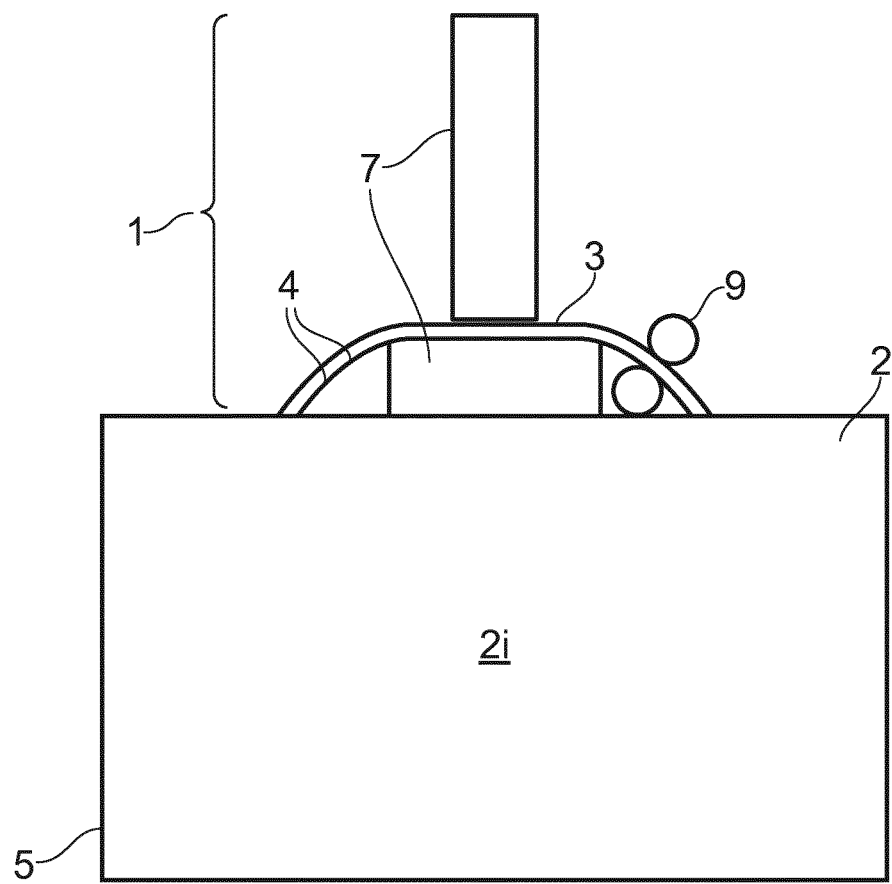
FIG. 2 illustrates an exemplary device (1) of the invention fluidly connected to a bioreactor (2) with a pump (9) promoting flow of liquid cell culture from the interior (2i) of a bioreactor (2) through the hollow body (3) of the device (1).

FIG. 2 is a schematic diagram of a similar exemplary configuration to that of FIG. 1 further comprises a pump (9) configured to promote flow of liquid cell culture from said bioreactor (2) through the hollow body (3) via said fluid path (5a-5b). In one embodiment the pump is a peristaltic pump positioned around either the upstream or the downstream conduit that acts to positively displace liquid cell culture from the bioreactor through the interior of the hollow body of the device of the invention.

Also indicated in FIGS. 1 and 2 is the sealing means (7) of the device disposed about the hollow body.

Any mechanism that results in a liquid tight or hermetically sealed section of the hollow body being formed may be used with the present invention, e.g. crimping, heat sealing, etc. In one embodiment the sealing means (7) may be a heat seal (17) as illustrated in the exemplary configuration of FIG. 3. The term "heat seal" relates to applying heat, and optionally also pressure, at defined position in order to seal off a section so that fluid flow no longer passes through the sealed area. Heat sealing can join two similar or the same materials together or can join dissimilar materials. In known embodiments, a heated die or a sealing bar is used to apply heat to a specific contact area in order to weld the materials together. In the present invention the materials are the outer walls of the hollow body. Suitably, where a heat seal is used as the sealing means of the invention, the liquid cell culture itself should be exposed to a minimum amount of heat so as not to disturb the content of the liquid cell culture.

Heat seal devices are well-known in the field of packaging, e.g. bags and blisters in the food and pharmaceutical industry. A non-limiting example of a sealing means suitable for use in the present invention may comprise a relatively small heat sealer. The sealing means of the invention in one embodiment is at least partially automated, e.g. by means of a timer or being foot-operated distal to the device. In one embodiment a direct contact method of heat sealing is used where a constantly heated die or sealing bar applies heat to a specific contact area or path to seal or weld the thermoplastics together. Operation of the heating element may be carried out by the release of a short burst of electricity through a resistance wire so that the heating element comes to a temperature effective to weld the thermoplastic tubing together at a defined point. The duration of heat sealing step must be selected carefully. If too short it will result in a weak seal and if too long the thermoplastic material will burn instead of melt and will also result in an inferior seal and potentially have a negative impact on the cell culture. The optimum temperature, pressure and duration of application will depend on the thermoplastic material in question and can be easily determined.

Figure 3:
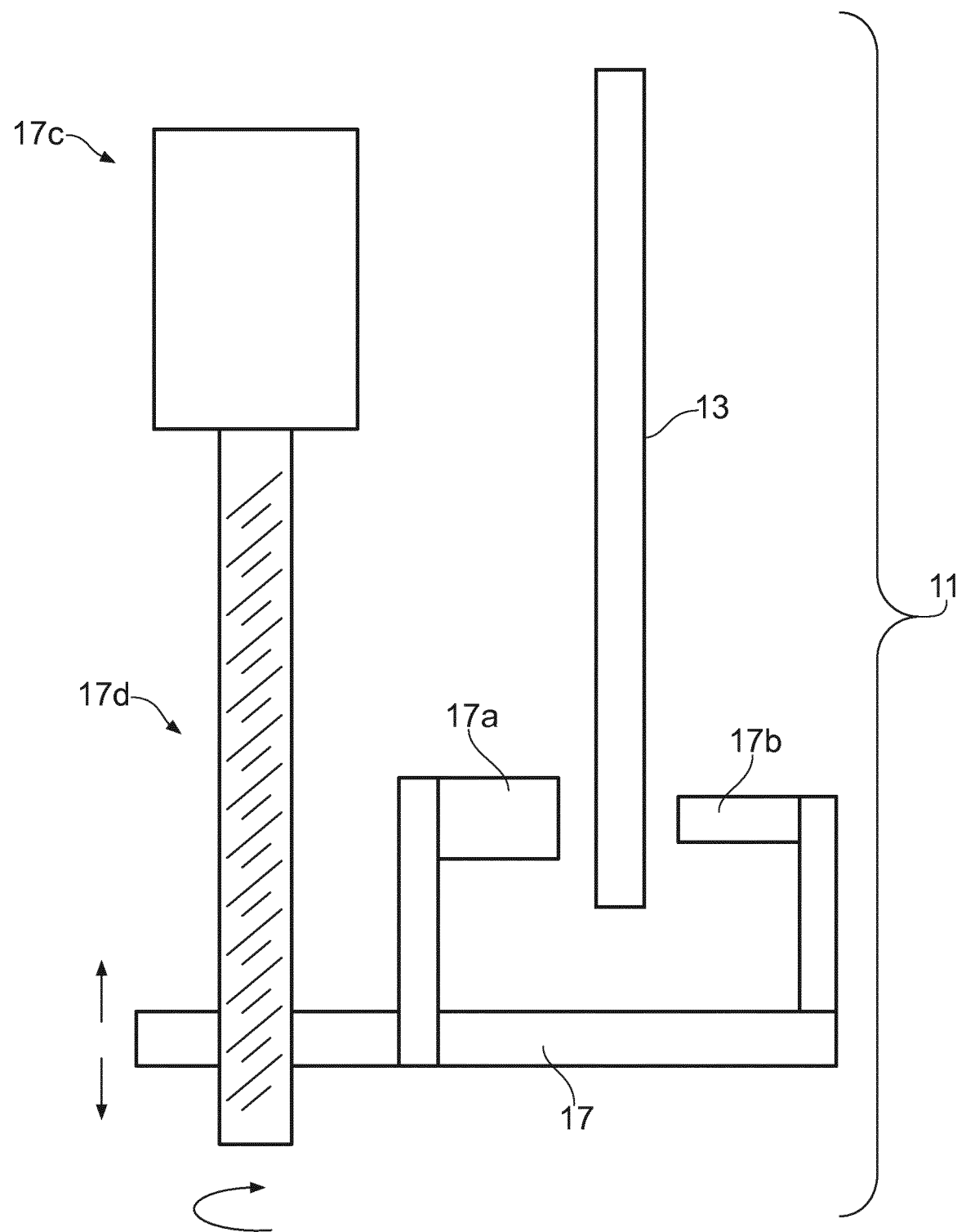
FIG. 3 illustrates an exemplary sealing means (17) suitable for use in a device (11) of the invention wherein first (17a) and second (17b) heatable dies are disposed about the hollow body (13) of the device (11).

FIG. 3 shows an exemplary embodiment of a suitable said heat seal (17), comprising a first (17a) and a second (17b) heatable die. As illustrated in FIG. 3 said heatable dies (17a, 17b) are disposed at opposing sides of said hollow body (13). In one embodiment these opposing faces of these dies are mirror images of each other and when brought together come into contact only at their perimeters, which suitably is the only part that is heated. In this way, when the opposing dies come together around the hollow body, a sealed section or bubble is formed containing a sample of said liquid cell culture. No fluid flow is permitted either into or out of this sealed section. The dies may take a variety of shapes but in one embodiment they may substantially form a sphere when brought together.

In one embodiment said sealing means (17), as for example shown in FIG. 3, is moveable along the length of said hollow body (13). In one embodiment a motor (17c) controls the movement of said sealing means (17). The motor (17c) in the embodiment illustrated in FIG. 3 is a fixed motor that acts in association with a worm gear (17d) in order to move the sealing means (17).

In one embodiment of the device (1) of the invention said sealable material is a thermoplastic material. The term "thermoplastic" refers to a material, typically a polymer, that becomes pliable or mouldable above a specific temperature, and returns to a solid state upon cooling. A variety of suitable thermoplastic materials is known to those of skill in the art, including similar materials to those recited hereinabove for the flexible plastic tubing. Non-limiting examples include PP, PE, PVC, nylon, PTFE and PEEK.

In one embodiment said hollow body (3) is formed completely from said thermoplastic material. In one embodiment said hollow body (3) is a flexible bag (13). FIG. 4-7 show an exemplary configuration wherein the hollow body is a flexible bag (13).

Figure 4:
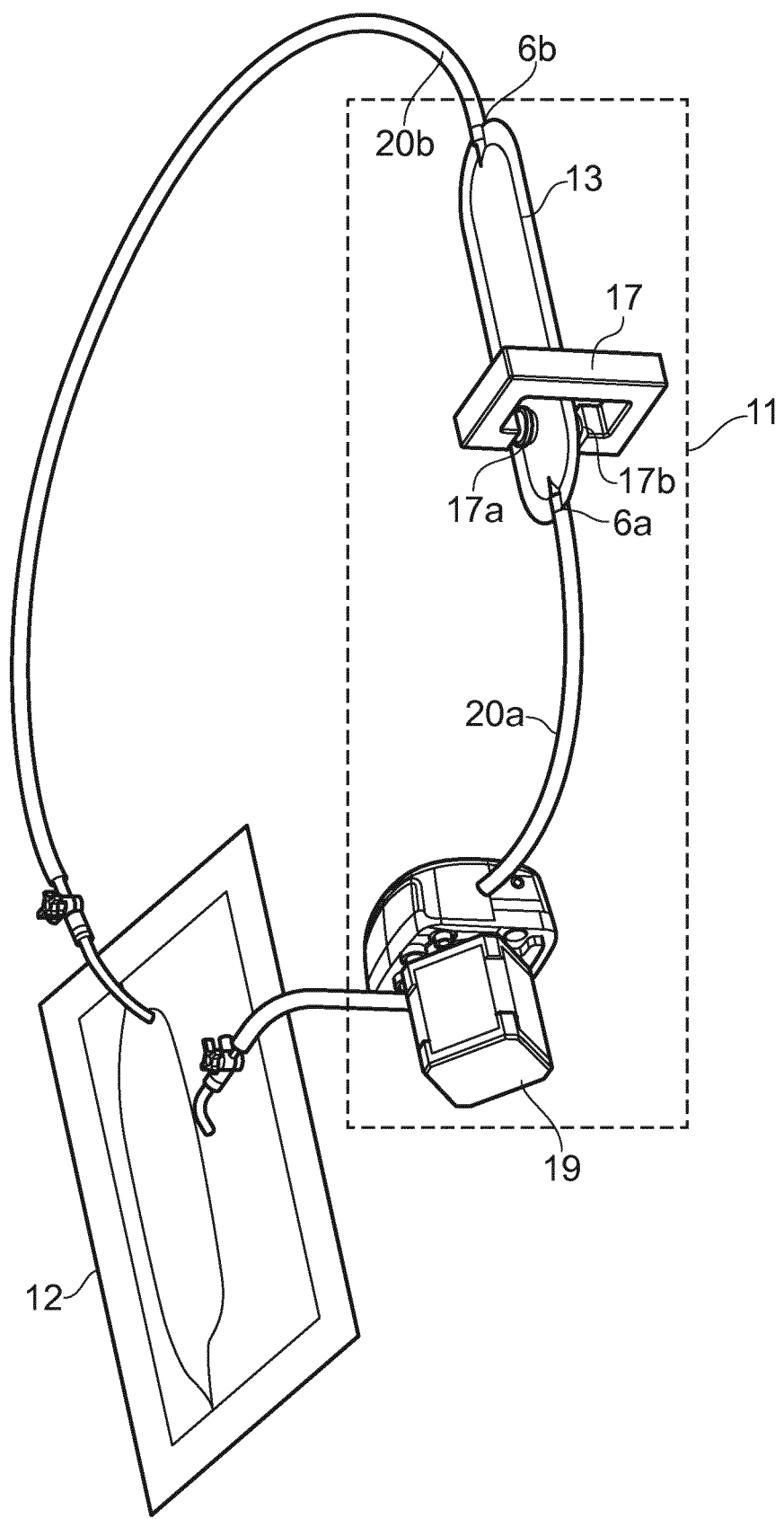
FIG. 4 shows an exemplary device (11) of the invention fluidly connected to a flexible bag bioreactor (12).
Figure 5:
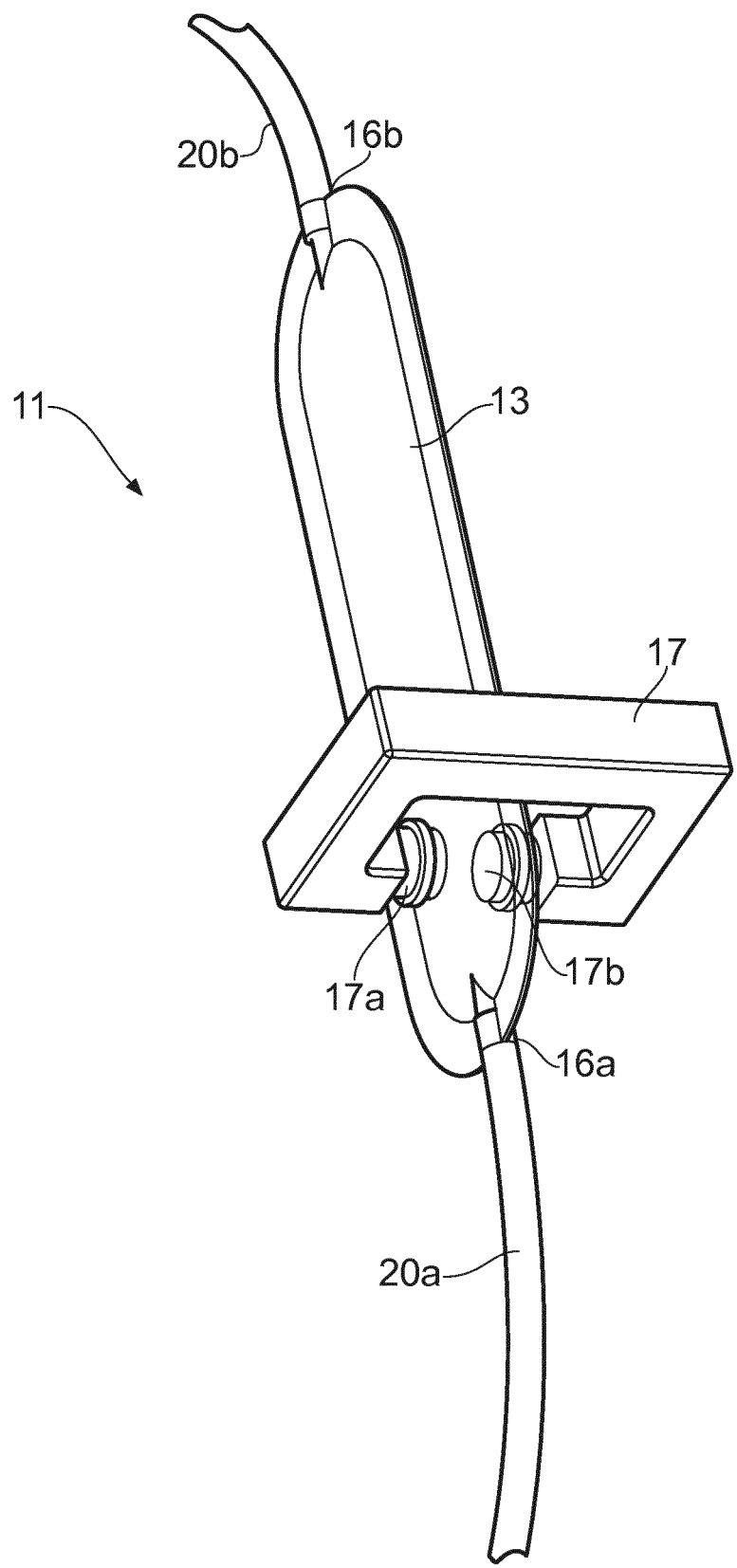
FIG. 5 is a closer view of the device (11) illustrated in FIG. 4 showing the spatial relationship between the hollow body (13) and the sealing means (17).
Figure 6:
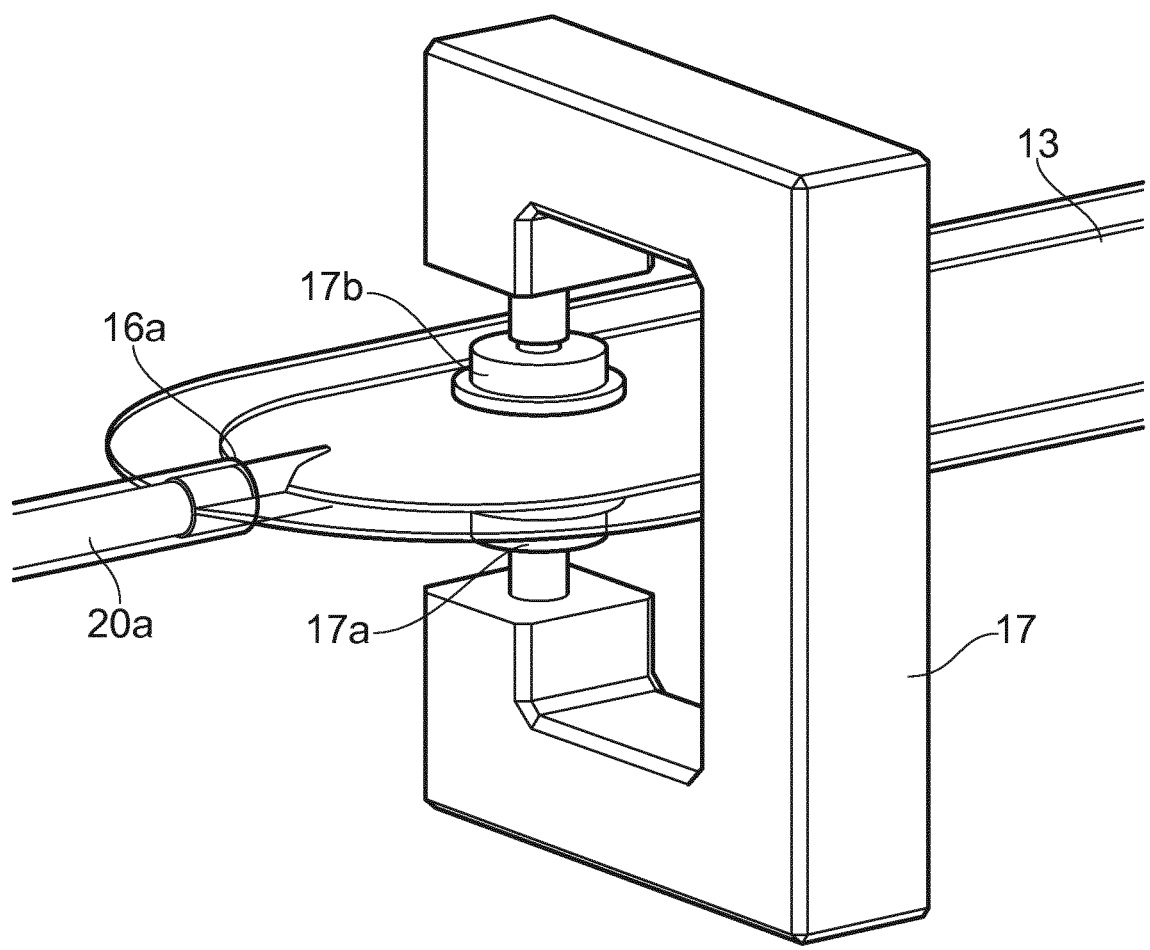
FIG. 6 is a view of a section of the device (11) of FIG. 4 illustrating how in one embodiment the first and second heatable dies (17a and 17b, respectively) are positioned on opposing sides of the hollow body (13).
Figure 7:
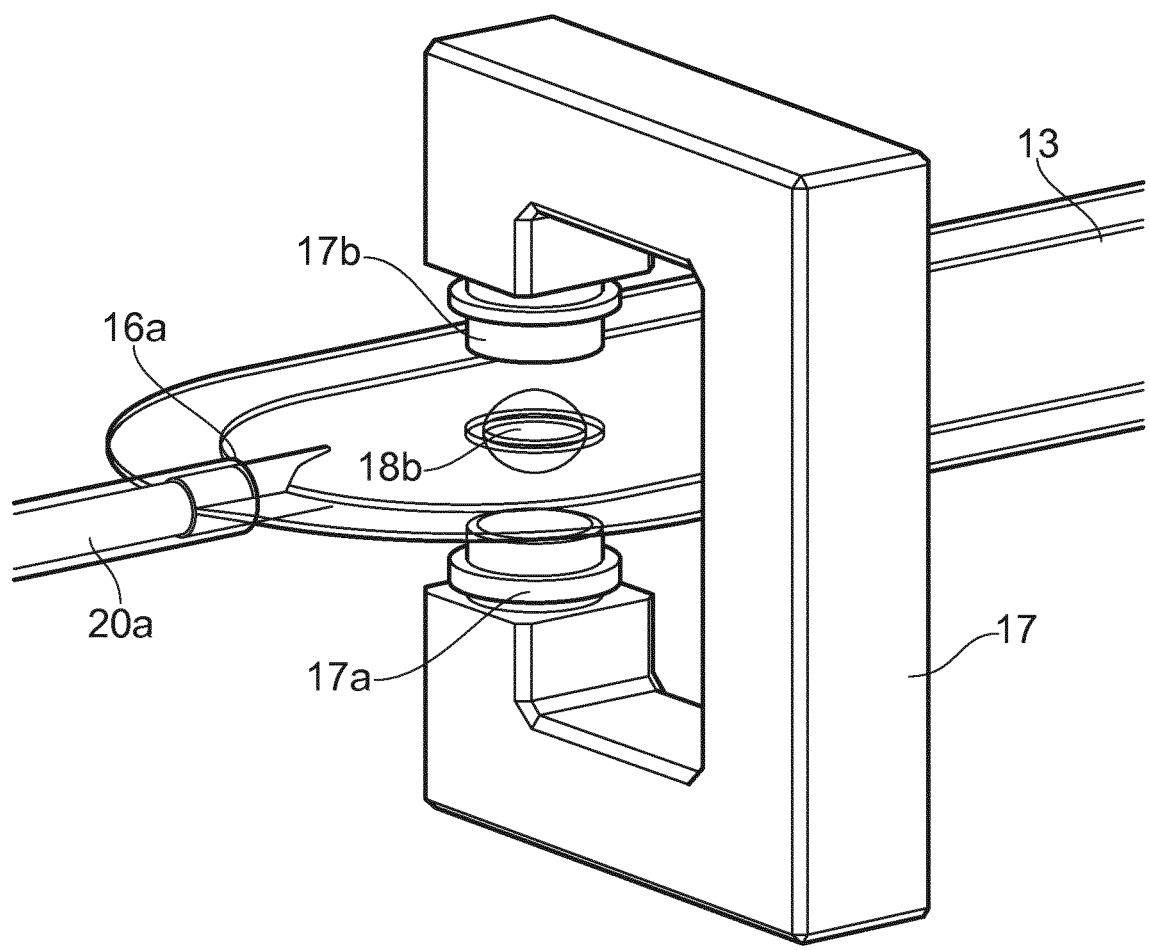
FIG. 7 illustrates the same view as FIG. 6 but where the heatable dies (17a and 17b, respectively) have been retracted after being brought together to produce a sealed section (18b) containing a sample of the liquid cell culture.

The exemplary device (11) of the invention illustrated in FIGS. 4-7 is intended to be supplied as a pre-sterilised single use disposable kit. The device (11) is assembled and positioned as illustrated. In certain embodiments the bioreactor in such a configuration is placed upon a rocking tray to facilitate cell culture, as is known in the art with systems such as the Xuri™ cell culture system. While loading the bioreactor onto a rocking tray, the sampling device (11) can be loaded into a sampling unit. As shown in FIG. 4, the upstream conduit (20a) can pass through a pump (19). In one embodiment the pump (19) can keep the upstream conduit (20a) pinched when not sampling to avoid any liquid cell culture transfer into the flexible bag (13) during rocking of the bioreactor (12).

In one embodiment of the method of the invention, sampling at a pre-set interval is initiated by tilting the bioreactor (12) to a sampling position. The flexible bag (13) is situated between two heatable dies (17a, 17b) in the form of cups ("heat seal cups") and liquid cell culture is allowed to pass through the flexible bag (13) and back to the bioreactor (12). The heat seal cups (17a, 17b) are brought close together to ultimately hold liquid cell culture in a cavity in the form of an unsealed bubble. Then the heat seal cups (17a, 17b) are heated to seal the periphery of the bubble and form a sealed section (18b) in the form of a bubble. The bioreactor thereafter moves back to its original non-sampling position. The heat seal cups (17a, 17b) then cool to room temperature and separate out to expose the sealed section (18b) and make it accessible for removal or for sampling therefrom in situ. The heat seal cups (17a, 17b) can move linearly to a subsequent position for a new sampling cycle.

Figure 8:
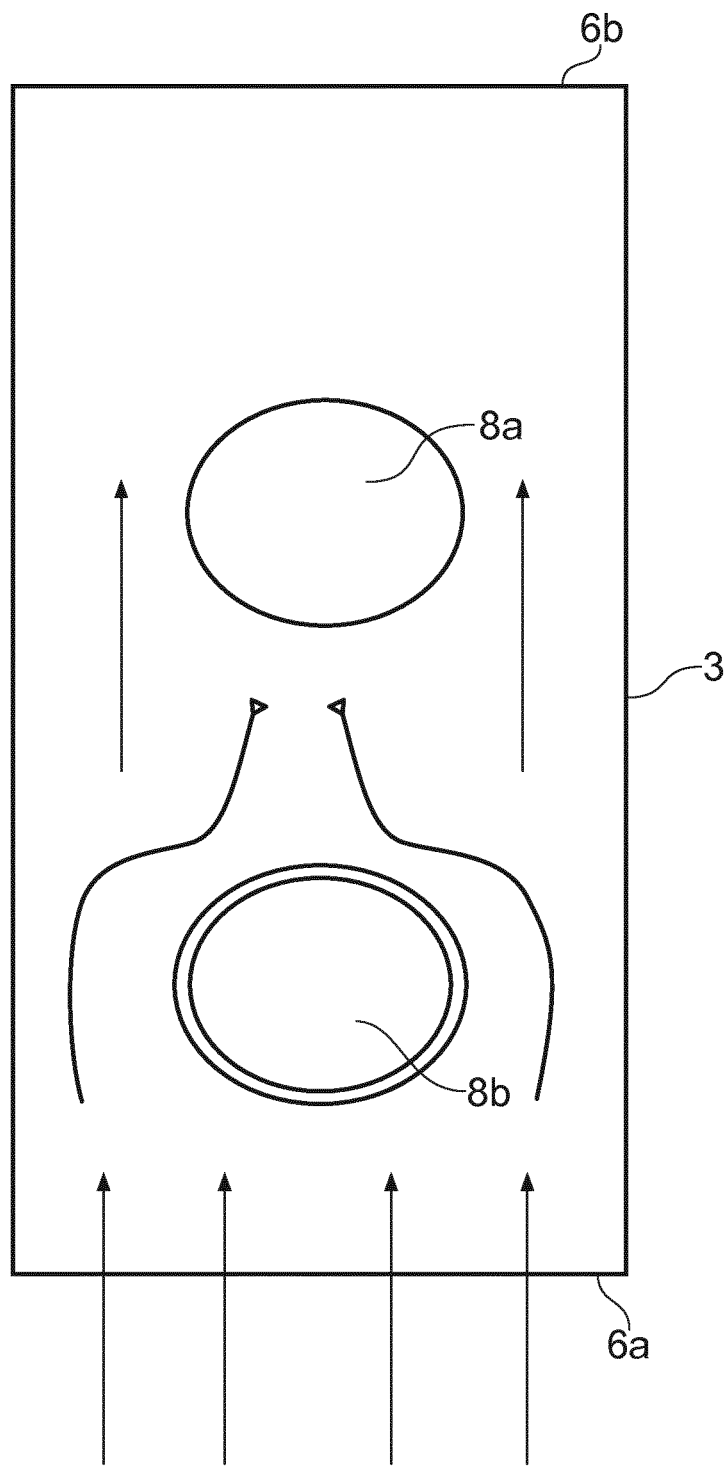
FIG. 8 is a diagram showing how liquid cell culture from a bioreactor flows through a device of the invention even after a section (8b) of the hollow body (3) has been sealed.

FIG. 8 is a schematic diagram of a hollow body (3) of the device of the invention showing how flow of liquid cell culture from the upstream end (6a) to the downstream end (6b) is not impeded when a sealed section (8b) has been formed.

Figure 9:
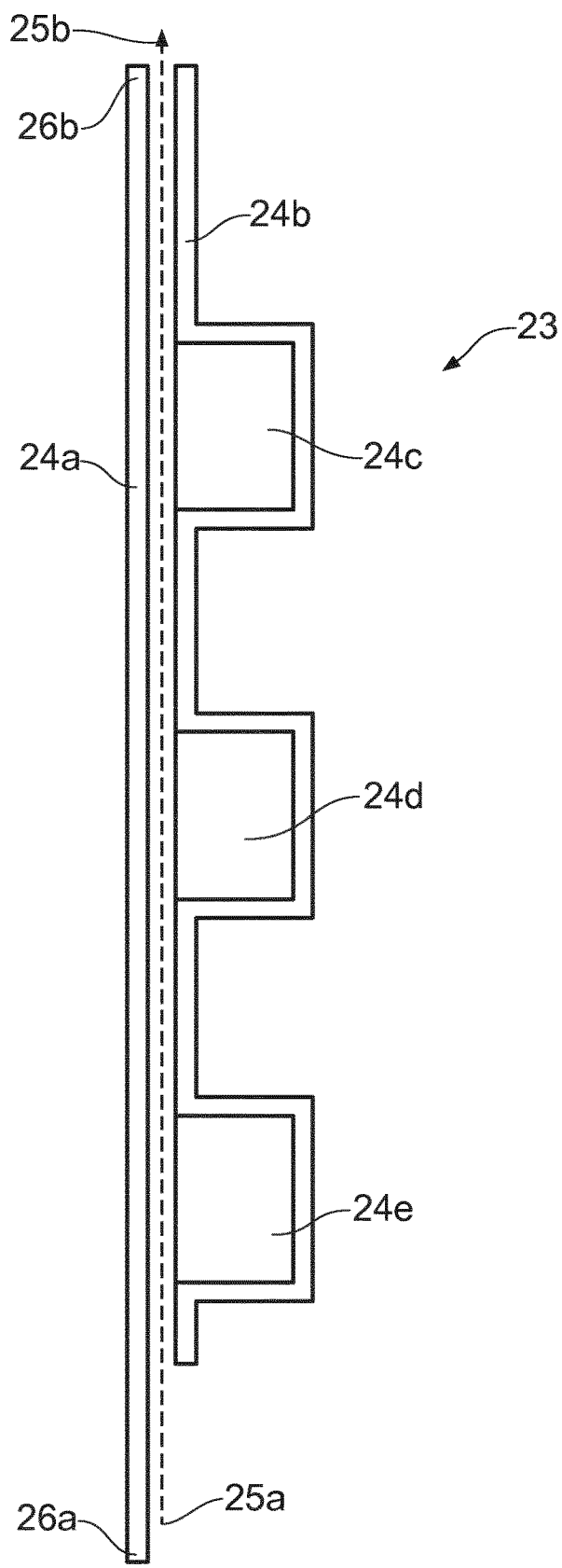
FIG. 9 illustrates an exemplary hollow body (23) suitable for the device of the invention comprising one wall (24a) made from a flexible material and another wall (24b) made from a rigid material and defining a plurality of wells (24c-e).
Figure 10:
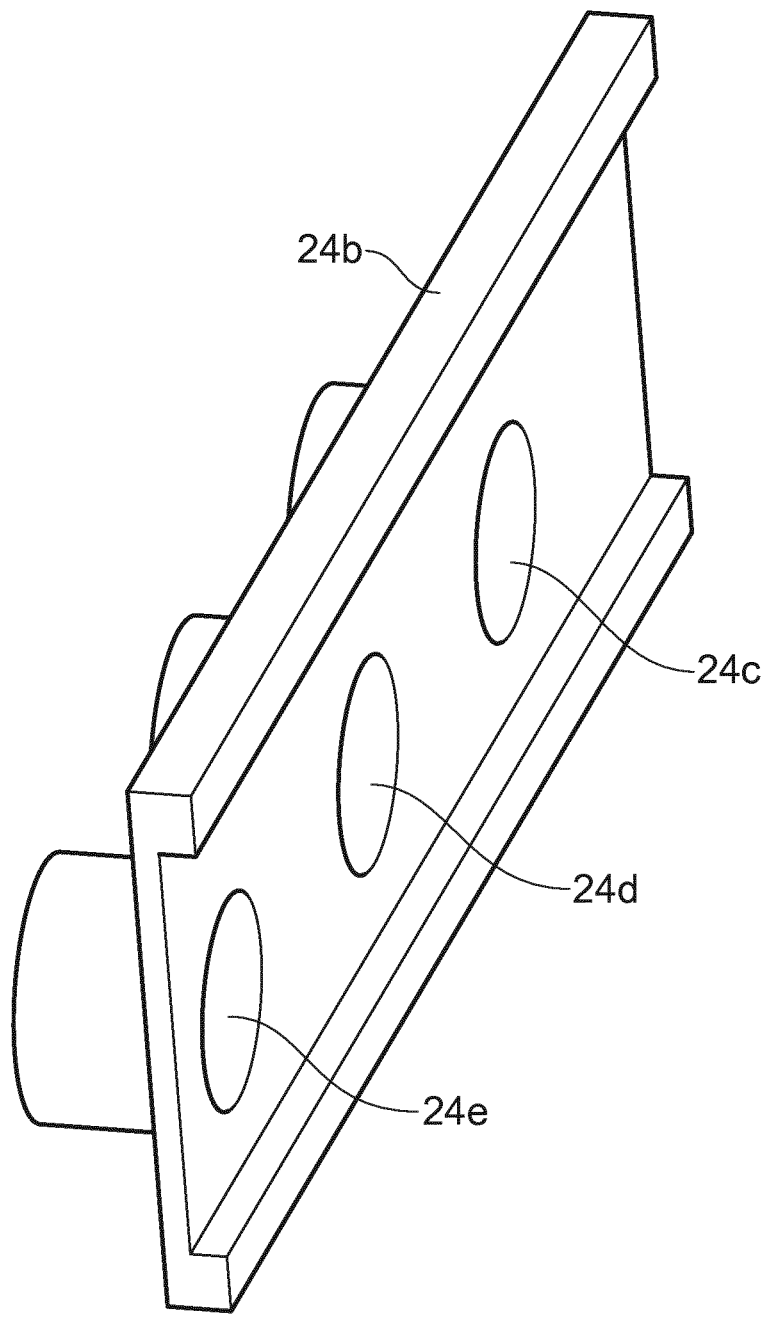
FIG. 10 is a substantially isometric view of the rigid wall (24b) from FIG. 9 where the openings of the wells (24c-e) can be seen.
Figure 11:
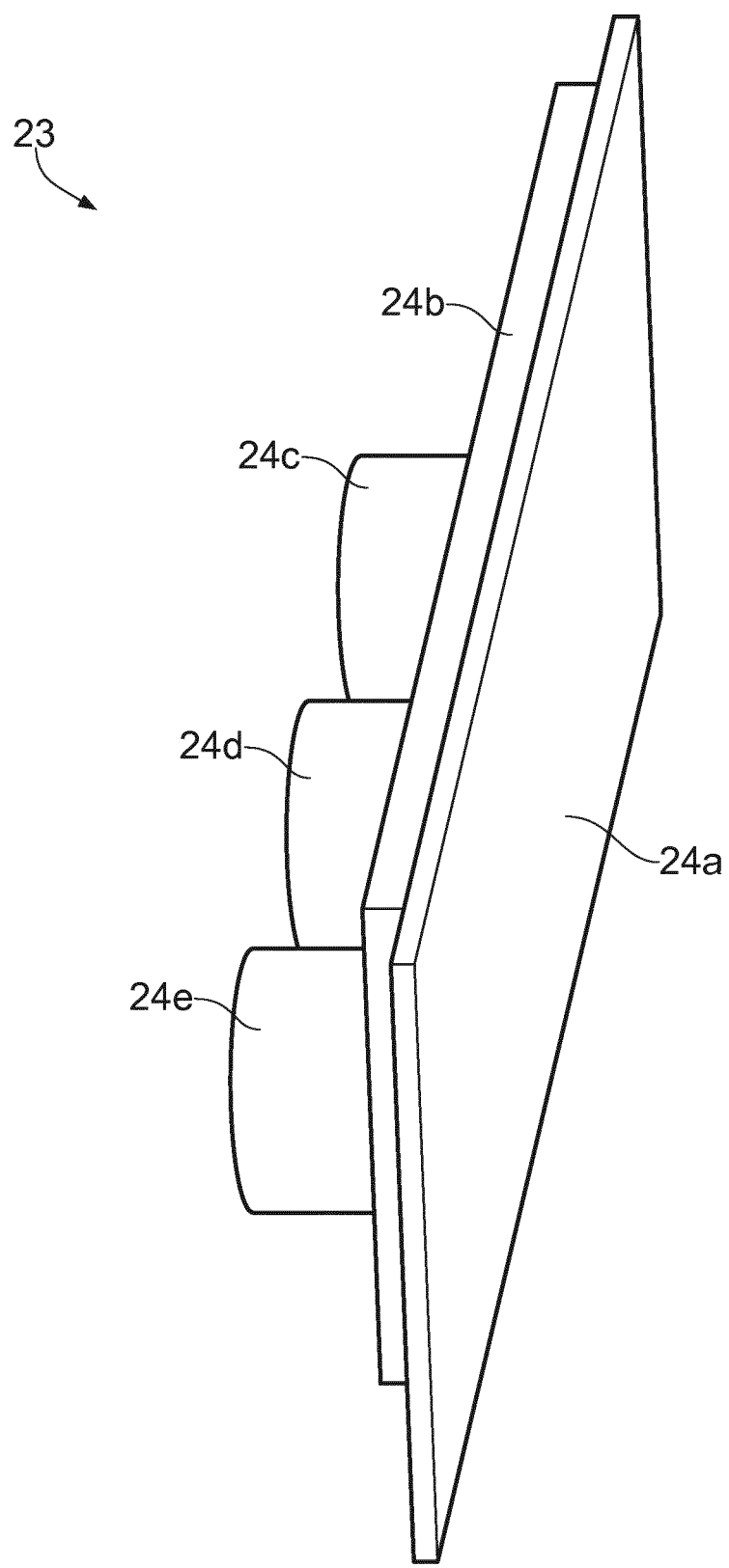
FIG. 11 is the same view as FIG. 10 but wherein the flexible wall (24a) has been secured to the rigid wall (24b) in order to form an exemplary hollow body (23) of the invention.

FIGS. 9-11 show an exemplary embodiment wherein said hollow body (23) is formed from a first wall (24a) formed from a thermoplastic material and a second wall (24b) formed from a substantially rigid material. In the configuration illustrated in FIGS. 9-11 said second wall (24b) defines a plurality of sampling wells (24c-e). Particularly suitable for this embodiment is when the second wall is formed from a substantially rigid material. In one embodiment the second wall is a typical multiwell plate.

In the exemplary embodiment illustrated in FIGS. 9-11 a second wall (24b) formed of a substantially rigid material is shown. This wall (24b) can be formed of a hard plastic (PP or other commonly used materials in bioprocess and cell therapy) which is injection moulded. This substantially rigid part has sampling wells (24c-e) or pockets for sample collection. In one embodiment the sampling wells (24c-e) are disposed at the top of the device and so that samples are not collected in the wells due to gravity. With this arrangement dead volume issues are avoided, which can affect real time samples and correctness of sample information which can otherwise be detrimental to the process. The first wall (24a) can be formed from a material similar to that used for bioreactor bags and tubes, e.g. as used with the Xuri™ bioreactor system. In one embodiment the material of the first wall can be silicon layers. The hollow body shown in FIGS. 9-11 can be prefabricated where the first wall (24a) is integrated with the second wall (24b) subsequent to injection moulding of the second wall (24b). The space between the first and second walls (24a, 24b) defines the fluid path (25a, 25b). A tubular sealer can act on the first wall (24a) to secure a sealed section or sample pocket. In one embodiment sampling is carried out when the downstream end (26b) is closed using a valve and a pump (valve and pump not shown in FIGS. 9-11) is running at the upstream end (26a) to effect sample collection under pressure inside the upward down wells. In this embodiment, subsequent to sample collection, the valve is opened and pump is run to avoid and dead zones.

Another aspect of the present invention is a method for taking a sample from a bioreactor containing a liquid cell culture. Any definition or embodiment of a feature of the device of the invention that is common to the method of the invention also applies to the method of the invention.

The phrase "activating said sealing means" as part of the method of the invention refers to those steps required for the sealing means to act upon the sealable material in order to produce a seal.

The term "seal" in the present invention refers to isolating a selected section of the hollow body so that it is fluidly sealed from the remainder of the interior of the system, i.e. the system comprising the device of the invention connected to a bioreactor.

The term "syringing" means removing a portion of liquid sample contained in a sealed section of the hollow body by means of a syringe. The method of doing so is well known to those of skill in the art. Suitably, a syringe used for this step should be sterile. Steps to sterilise and to maintain sterility are well known to those of skill in the art.

The step of "separating said sealed section" refers to taking the sealed section away from the device of the invention without disturbing the flow of liquid cell culture from the bioreactor through the device of the invention. In other words, a fluid-tight seal must remain around the place from where the sealed section has been removed. The sealed section, or volume of sample, can be taken to a laboratory bench to process.

The phrase "relocating said sealing means" refers to the act of moving the sealing means to a place around or near to the hollow body that has not been previously acted upon by the sealing means. This permits a subsequent sampling to be carried out.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. A device for taking a sample from a liquid cell culture in a bioreactor wherein said device comprises:
   (i) a hollow body comprising outer walls that define a fluid path therethrough wherein said outer walls are at least partly comprised of a sealable material, wherein said fluid path begins at an upstream end of said hollow body, through said hollow body, and ends at a downstream end of said hollow body, and wherein said upstream and downstream ends are adapted to fluidly connect said fluid path with an interior of said bioreactor, wherein the liquid cell culture flows from the interior of said bioreactor into the fluid path via the upstream end and flows back to the interior of said bioreactor via the downstream end; and,
   (ii) a sealer which is adapted to seal a perimeter of a section of said sealable material without blocking said fluid path during the liquid cell culture passing through the fluid path, wherein said sealer is moveable between different portions of said outer walls.

2. The device as defined in claim 1, wherein an upstream conduit fluidly connects the interior of said bioreactor with said fluid path via said upstream end of said device and a downstream conduit fluidly connects the interior of said bioreactor with said fluid path via said downstream end of said device.

3. The device as defined in claim 2, wherein said upstream conduit and said downstream conduit are formed from plastic tubing.

4. The device as defined in claim 1 which further comprises a pump configured to promote flow of liquid cell culture from said bioreactor through said fluid path.

5. The device as defined in claim 1, wherein said sealer is a heat seal.

6. The device as defined in claim 5, wherein said heat seal comprises first and second heatable dies.

7. The device as defined in claim 6, wherein said first and second heatable dies are disposed at opposing sides of said hollow body.

8. The device as defined in claim 1, wherein said sealer is moveable along a length of said hollow body.

9. The device as defined in claim 8, wherein a motor controls a movement of said sealer.

10. The device as defined in claim 1, wherein said sealable material is a thermoplastic material.

11. The device as defined in claim 10, wherein said hollow body is formed completely from said thermoplastic material.

12. The device as defined in claim 1, wherein said hollow body is a flexible bag.

13. The device as defined in claim 1, wherein said hollow body is formed from a first wall formed from a thermoplastic material and a second wall formed from a substantially rigid material.

14. The device as defined in claim 13, wherein said second wall defines a plurality of sampling wells.

15. A method for taking a sample from a bioreactor containing a liquid cell culture wherein said method comprises:
   (a) providing a device as defined in claim 1 fluidly connected to said bioreactor; and,
   (b) activating said sealer to seal a section of said sealable material without blocking said fluid path wherein said section contains the sample of said liquid cell culture.

16. The method as defined in claim 15 which further comprises (c) removing some or all of said sample from said sealed section.

17. The method as defined in claim 16, wherein said removing comprises syringing some or all of said sample out of said sealed section.

18. The method as defined in claim 16, wherein said removing comprises separating said sealed section from said device.

19. The method as defined in claim 16 which further comprises (d) of relocating said sealer about a new section of said sealable material.

20. The method as defined in claim 19, further comprising repeating (b) to seal the new section.

21. The method as defined in claim 20, further comprising repeating (c) to remove sample from the new sealed section.

22. The method as defined in claim 15 which is automated.

\* \* \* \* \*